United States Patent [19]
Muchin

[11] Patent Number: 6,058,931
[45] Date of Patent: *May 9, 2000

[54] NASAL DILATOR

[75] Inventor: Jerome D. Muchin, Los Angeles, Calif.

[73] Assignee: Acutek International, Inglewood, Calif.

[*] Notice: This patent is subject to a terminal disclaimer.

[21] Appl. No.: 08/996,056

[22] Filed: Dec. 22, 1997

Related U.S. Application Data

[63] Continuation of application No. 08/698,002, Aug. 16, 1996, Pat. No. 5,718,224, application No. 08/580,127, Dec. 28, 1995, Pat. No. 5,611,334, application No. 08/521,631, Aug. 31, 1995, Pat. No. 5,553,605, and application No. 08/499,636, Jul. 7, 1995, Pat. No. 5,546,929.

[51] Int. Cl.$^7$ .................................................. A61M 15/00
[52] U.S. Cl. ...................... 128/200.24; 606/199
[58] Field of Search .................. 128/200.24, 207.18; 606/204.45, 199

[56] References Cited

U.S. PATENT DOCUMENTS

| | | |
|---|---|---|
| Re. 35,408 | 12/1996 | Petruson . |
| 142,477 | 9/1873 | James . |

(List continued on next page.)

FOREIGN PATENT DOCUMENTS

| | | |
|---|---|---|
| 242553 | 5/1961 | Australia . |
| 0 333 749 B1 | 9/1989 | European Pat. Off. . |
| 0 375 810 A1 | 7/1990 | European Pat. Off. . |
| 394505 | 3/1909 | France . |
| 630889 | 12/1927 | France . |
| 1001434 | 2/1952 | France . |
| 1046299 | 12/1953 | France . |
| 1182602 | 6/1959 | France . |
| 1351537 | 12/1962 | France . |
| 381127 | 9/1923 | Germany . |
| 437661 | 11/1926 | Germany . |
| 453006 | 3/1928 | Germany . |
| 882601 | 7/1953 | Germany . |
| 3640979 A1 | 8/1987 | Germany . |
| 4 030 465 A1 | 4/1992 | Germany . |
| 289561 | 10/1985 | Spain . |
| 2504 | 11/1910 | United Kingdom . |
| 18254 | 11/1911 | United Kingdom . |
| 354998 | 8/1931 | United Kingdom . |
| 520491 | 4/1940 | United Kingdom . |
| 748326 | 4/1956 | United Kingdom . |
| 768488 | 2/1957 | United Kingdom . |
| 786488 | 11/1957 | United Kingdom . |
| 1 244 146 | 8/1971 | United Kingdom . |
| 1 435 853 | 5/1976 | United Kingdom . |

(List continued on next page.)

OTHER PUBLICATIONS

Bollinger Article "Airflo™ Adhesive Nose Strips".

(List continued on next page.)

*Primary Examiner*—Aaron J. Lewis
*Attorney, Agent, or Firm*—Oppenheimer, Wolff & Donnelly LLP

[57] ABSTRACT

A nasal dilator for preventing outer wall tissue of nasal passages of a nose from drawing in during breathing. There is a spring member for bridging a human nose, the spring member extending over the bridge and at least partly beyond the bridge on both sides of the bridge. A pad having a flexible section of lesser resilience than the spring, and with an adhesive surface covers the spring member and extends around the spring member so that there is a perimeter of space formed between the spring member and the pad member. The spring is inset centrally in the pad. An adhesive between the spring member and the pad wholly connects the spring member on its entire engaging surface with the pad. The edges of the pad can lift from the nose. The dilator can be formed of transparent or clear material so as to enhance its cosmetic appearance on the nose, and there can be printing on one or more members of the dilator. The dilator can be preset before use by establishing a contrary curvature, or the flexible pad can be stretched before adherence to the pad.

5 Claims, 4 Drawing Sheets

U.S. PATENT DOCUMENTS

| | | |
|---|---|---|
| D. 310,565 | 9/1990 | Petruson . |
| 701,538 | 6/1902 | Carence . |
| 850,978 | 4/1907 | Soares . |
| 1,043,924 | 11/1912 | Gottlieb . |
| 1,134,993 | 4/1915 | Bye . |
| 1,256,188 | 2/1918 | Wilson . |
| 1,292,083 | 1/1919 | Sawyer . |
| 1,322,375 | 11/1919 | Un . |
| 1,950,839 | 3/1934 | Chirila . |
| 1,950,926 | 3/1934 | Lobl . |
| 2,001,862 | 5/1935 | Battey . |
| 2,055,855 | 9/1936 | Weaver . |
| 2,221,758 | 11/1940 | Elmquist . |
| 2,243,360 | 5/1941 | Slatis et al. . |
| 2,264,153 | 11/1941 | Rowe . |
| 2,273,873 | 2/1942 | Klein . |
| 2,274,997 | 3/1942 | Thurman . |
| 2,277,390 | 3/1942 | Crespo . |
| 2,398,073 | 4/1946 | Bonde . |
| 2,426,161 | 8/1947 | Biederman . |
| 2,509,157 | 5/1950 | Lind . |
| 2,566,148 | 8/1951 | Sky . |
| 2,586,219 | 2/1952 | Geffas . |
| 2,625,931 | 1/1953 | Phillips . |
| 2,674,245 | 4/1954 | Tanditter . |
| 2,715,904 | 8/1955 | Hill . |
| 2,949,443 | 8/1960 | Merriam et al. . |
| 3,027,897 | 4/1962 | Carofiglio . |
| 3,046,989 | 7/1962 | Hill . |
| 3,426,751 | 2/1969 | Radewan . |
| 3,531,090 | 9/1970 | Laible . |
| 3,742,943 | 7/1973 | Malmin . |
| 3,747,597 | 7/1973 | Olivera . |
| 3,802,426 | 4/1974 | Sakamoto . |
| 3,835,848 | 9/1974 | Berner . |
| 3,905,335 | 9/1975 | Kapp . |
| 3,935,859 | 2/1976 | Doyle . |
| 4,153,051 | 5/1979 | Shippert . |
| 4,181,127 | 1/1980 | Linsky et al. . |
| 4,201,217 | 5/1980 | Slater . |
| 4,213,452 | 7/1980 | Shippert . |
| 4,220,150 | 9/1980 | King . |
| 4,221,217 | 9/1980 | Amezcua . |
| 4,267,831 | 5/1981 | Aguilar . |
| 4,274,402 | 6/1981 | Shippert . |
| 4,324,237 | 4/1982 | Buttaravoli . |
| 4,327,719 | 5/1982 | Childers . |
| 4,340,040 | 7/1982 | Straith . |
| 4,341,207 | 7/1982 | Steer et al. . |
| 4,341,208 | 7/1982 | Gordon . |
| 4,402,314 | 9/1983 | Goode . |
| 4,414,977 | 11/1983 | Rezakhany . |
| 4,440,231 | 4/1984 | Martin . |
| 4,485,809 | 12/1984 | Dellas . |
| 4,534,342 | 8/1985 | Paxa . |
| 4,592,357 | 6/1986 | Ersek . |
| 4,669,458 | 6/1987 | Abraham et al. . |
| 4,674,133 | 6/1987 | Oschner . |
| 4,744,355 | 5/1988 | Faasse, Jr. . |
| 4,823,789 | 4/1989 | Beisang, III . |
| 4,917,112 | 4/1990 | Kalt . |
| 4,932,943 | 6/1990 | Nowak . |
| 4,971,282 | 11/1990 | Dickinson . |
| 4,984,302 | 1/1991 | Lincoln . |
| 4,995,114 | 2/1991 | Price, Jr. . |
| 5,003,971 | 4/1991 | Buckley . |
| 5,022,389 | 6/1991 | Brennan . |
| 5,067,482 | 11/1991 | Reid . |
| 5,101,837 | 4/1992 | Perrin . |
| 5,116,675 | 5/1992 | Nash-Morgan . |
| 5,209,801 | 5/1993 | Smith . |
| 5,284,469 | 2/1994 | Jasen et al. . |
| 5,383,891 | 1/1995 | Walker . |
| 5,466,456 | 11/1995 | Glover . |
| 5,476,091 | 12/1995 | Johnson . |
| 5,479,944 | 1/1996 | Petruson . |
| 5,533,499 | 7/1996 | Johnson . |
| 5,533,503 | 7/1996 | Doubek et al. . |

FOREIGN PATENT DOCUMENTS

| | | |
|---|---|---|
| 2 126 101A | 3/1984 | United Kingdom . |
| 2 217 206A | 10/1989 | United Kingdom . |
| WO88/03788 | 6/1988 | WIPO . |
| WO91/18567 | 12/1991 | WIPO . |
| WO92/22340 | 12/1992 | WIPO . |
| WO94/23675 | 10/1994 | WIPO . |

OTHER PUBLICATIONS

Petruson, Bjorn; "Improvement of the Nasal Airflow by the Nasal Dilator Nozovent", *Rhinology*, vol. 26, pp. 289–222 (1988).

Petruson, Bjorn; Letter to the Editor; "Better Sleep with Dilated Nose", *Rhinology*, vol. 27, pp. 211–213 (1989).

Petruson, Bjorn; "Decreased Nasal Resistance by the Nasal Dilator Nozovent® can Reduce Snoring", World Congress on Chronic Rhonchopathy, pp. 1–4 (May 1989).

Hoijer, Ulf et al.; "The Effects of Nasal Dilation on Snoring and Obstructive Sleep Apnea", *Archives of Ortolarngology– –Head & Neck Surgery*, vol. 118, pp. 281–284 (Mar. 1992).

Petruson, Bjorn; "Snoring Can be Reduced When the Nasal Airflow is Increased by the Nasal Dilator Nozovent", *Archives of Ortolarngology–Head & Neck Surgery*, vol. 116, pp. 462–464 (April 1990).

Petruson et al.; The Importance of Nose–Breathing for the Systolic Blood Pressure Rise During Exerise;, *Acta Otolaryngol*, Stockholm vol. 109, pp. 461–466 (1990).

E.N.T. Spring Symposium; "Report of a Symposium at the Royal Society of Medicine, London, May 21, 1991", pp., 1–4.

Petruson et al.; "Two New Ways for Nasal Administratiuon of Drugs with the Nasal Dilator Nozovent", Abstract, ENT–Department , University of Goteberg, Sahlgren's Hospital, 413, 45 Goteborg, Sweden.

Ford, C.N. et al.; "A Nasal Prosthesis for Treatment of Nasal Airway Obstruction", *Rhinology*, vol. 23, pp. 223–229 (1985).

J.M. Lancer and A.S. Jones; "The Francis Alae Nasi Prop and Nasal Resistance to Airflow", *Journal of Laryngol, Otol.*, vol. 100, pp.539–541 (1986).

Foreign language newspaper article, "Adne Har Nese. . . " (undated).

Foreign language newspaper article, "Edna Raskere Med Ring I Nesen?" (undated).

Foreign language newspaper article, "Skoytelopere Med Ring I Nesen. . . " (undated).

foreign language magazine artile, "Sagen in Der Nacht" (undated) (see entire document).

NASAL DILATOR

RELATED APPLICATIONS

This application is a continuation of U.S. application Ser. No. 08/698,002 filed Aug. 16, 1996 and issued as U.S. Pat. No. 5,718,224; U.S. application Ser. No. 08/580,127 filed Dec. 28, 1995 and issued as U.S. Pat. No. 5,611,334; U.S. Ser. No. 08/521,631 filed Aug. 31, 1995 and issued as U.S. Pat. No. 5,553,605; and U.S. Ser. No. 08/499,636 filed Jul. 7, 1995 and issued as U.S. Pat. No. 5,546,929.

BACKGROUND

This invention relates to dilators for the nose. In particular, the invention is concerned with a dilator to urge the nasal passages of the nose open during breathing.

One known form of dilator used for this purpose is in the nature of a band for extension over the nose from one nasal passage, over the bridge of the nose, to the other nasal passage. This pad is formed of a flexible material which has sandwiched with it a resilient spring material. Both the flexible material and the spring are normally planar. When the pad is placed on the nose, it sticks to the skin of the nose, and the action of the spring causes the nasal passages to be urged open.

In the Applicant's experience, the known dilator is not as effective as it could be. In particular, the nasal passages are not urged open as much or as little as they could usefully and safely be opened. Also, the currently known device consists of multiple components forming the pad in a sandwich relationship with the spring. Therefore, the fabrication of such a dilator arrangement is unduly complicated.

There is a need to provide a pad system for a dilator for location over the nose which minimizes the disadvantages of known systems.

SUMMARY

By this invention there is provided a dilator which has advantages over known dilators.

According to the invention, there is provided a nasal dilator for preventing outer wall tissue of nasal passages of a human nose from drawing in during breathing. The dilator includes an elongated resilient spring member for bridging a human nose, and there is also a flexible pad having a surface area and peripheral edge. The pad, which is made of a breathable material, engages the spring member, which is a polyflex material, and extends around the spring member.

There is an adhesive between the spring member and the pad such that the spring member on one of its entire engaging surface wholly adheres with the pad. A surface perimeter area of the pad is formed between the outer edge of the spring member and the peripheral edge of the pad. The surface perimeter area includes an adhesive for adhering to skin of the nose.

When the spring member is located over the bridge of the nose, the opposite flat surfaces of the spring member extend over the bridge of the nose and at least partly beyond the bridge of the nose. In this manner, the spring extends over the nasal passages on both sides of the bridge.

In some embodiments, when in use on the nose, there are only the spring member, the adhesive pad, and the adhesive between the pad and the spring member. When in position on the nose, a flat surface of the spring member engages directly on the nose. In some other embodiments, there is also an adhesive on the surface area of the spring adjacent to the bridge of the nose, so the spring member adheres to the nose.

In different embodiments, there are situations where at least one of, and preferably all of the components, namely pad, adhesive and spring are substantially transparent or clear, a flesh-like color or shade so as to effectively blend with the skin of wearer, or translucent. In other preferred situations the pad is effectively colored or rendered ornate or patterned, at least on its surface removed from the nose.

The dilator can be at least partly formed of transparent or clear material so as to enhance its cosmetic appearance on the nose. Ornamentation can be provided to one surface of the spring thereby to be visible through a transparent pad. Alternatively or additionally, the pad can be imprinted with ornamentation.

In yet other preferred forms of the invention, the pad is substantially transparent, and the spring is colored or patterned on its surface removed from the nose. The pattern can be a product logo. Coloring can represent a team color. The spring can be at least partly visible through the pad.

When unattached to the nose, the spring member and pad, has a natural position contrary to a curvature formed by location of the spring member over the bridge of the nose and adjacent to the nasal passages. Preferably, the natural position is with a curvature contrary to the shape of the curvature formed from one nasal passage over the bridge to the second nasal passage. The contrary curvature acts to place an increased amount of spring action on the dilator so that the dilation action on the nasal passages is enhanced when in use.

In one form of the invention, the dilator is located in a package before usage on the nose, and the interaction of the package on the dilator develops the contrary curvature. In another form of the invention, the pad is stretched prior to adhering to the spring, and that stretch acts to place the contrary curvature onto the dilator.

The invention is further described with reference to the accompanying drawings.

DRAWINGS

DESCRIPTION

Figure 1:
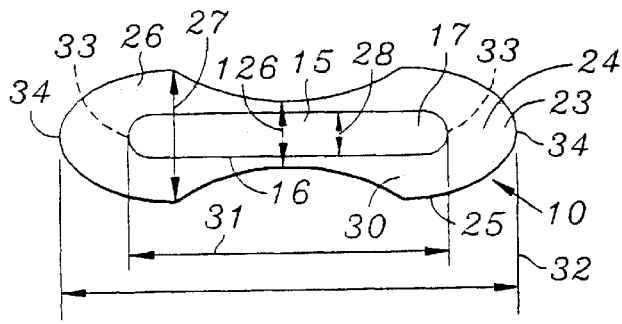
FIG. 1 is an underview of the dilator showing adhesive on the pad and on the spring.

A nasal dilator 10 prevents the outer wall tissue 11 of first and second nasal passages 12 and 13, respectively, of a human nose 14 from drawing in during breathing.

SPRING

The dilator 10 includes an elongated resilient spring 15 for bridging the human nose 14. The spring member 15 is formed of a synthetic resinous material. The spring member 15 has an outer edge 16 and opposite flat surfaces 17 and 18. The surface 17 extends over a bridge 19 of the nose 14.

The spring material 15 is formed of 0.010" clear polyester film. An acrylic adhesive carrier 20 having a thickness of 0.0015" liner for die cutting is provided on both sides. The adhesive is indicated by numerals 21 and 22.

In other situations, the film is white or colored at least on the surface 18. The surface 18 can have a logo pattern 118 printed on the face. Alternatively, different patterns, shapes, words, and letters can be used.

The film 15 is clear, durable, and has dimensional stability. It is resistant to mild acids, alkalis, and salt. Further, the film 15 is fungus, water and corrosion-resistant.

PAD

The dilator 10 includes a flexible adhesive pad 23 having a surface area 24 and peripheral edge 25. The pad 23 engages the spring member 15 and extending around the spring member 15.

The pad material 23 is preferably 9906T, 3M Elastic Nonwoven Tape from 3M Company, 3M Center, St. Paul, Minn. The product is a tan elastic polyurethane tape coated on one side with an acrylate adhesive 26. The tape is supplied on a paper liner 152 with the liner on the inside of the roll.

In other situations, the pad material is substantially transparent, clear or colored, for instance, to conform to a flesh color or tone.

Figure 11:
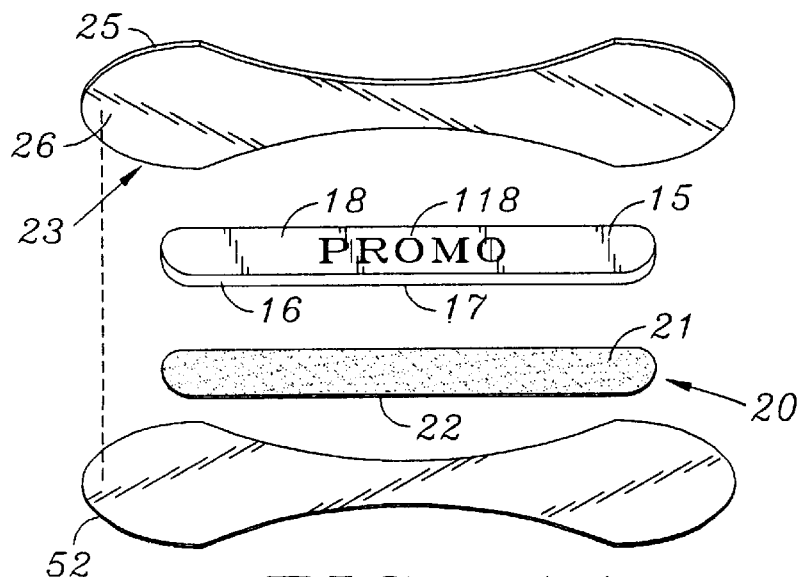
FIG. 11 is an exploded perspective top view of the components making up the dilator.

As shown in FIG. 11, when the pad 23 is transparent and the spring is colored, patterned or imprinted with a logo or the like, this imprintation is visible through the transparent pad 23. Thus, when worn on the nose 14, there is the appearance of a colored device, in part in whole, or of different combinations of pad and spring. The spring can thus be used as carrier of a message and not only for its resilient characteristics.

Figure 10A:
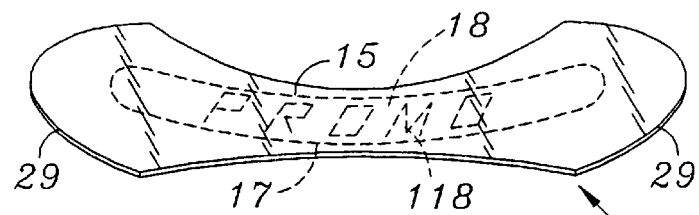
FIG. 10A is a perspective view from the top of the dilator before being placed on the nose, namely a counter-curved dilator, with an ornamentation on a surface of a spring being visible through the transparent pad.
Figure 10B:
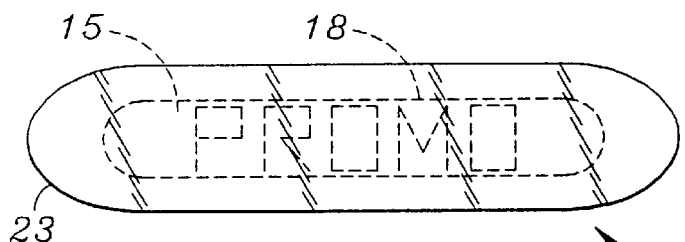
FIG. 10B is a perspective view of a second form of the dilator namely a flat substantially planar dilator before being placed on the nose. There is ornamentation on the spring visible through a transparent pad.

There is an arrangement shown in FIG. 10B which uses a dilator in a flat state before use on the nose. Also the pad 23 is tone or colored and imprinted 218 with a logo.

The backing of the tape is nonwoven of tan-colored polyurethane fibers. The adhesive is a hypoallergenic, pressure-sensitive acrylate. The liner is a silicone-coated kraft paper.

SPRING AND PAD

The spring member 15 occupies about 25% to about 50% of the surface area 24 of the pad 23. The spring member 5 is centrally located in the surface area 24 of the pad 23.

The peripheral edge 25 of the pad 23 defines a narrow width 26 and a broad width 27. The narrow width 26 is substantially for location over the bridge 19 of the nose 14. The broad width 27 is substantially for location centrally over the nasal passages 12 and 13 of the nose 14.

The spring member 15 defines a width 28. The width 28 of the spring member 15 being about one-half to three-quarters of the width of narrow width 26 of the pad 23. The pad 23 is an elongated element with rounded ends 29.

The spring member 15 defines a length 31 and the pad 23 defines a length 32. The spring member 15 is centrally located along the length 32 of the pad 23. The length 31 of the spring member 15 is between about one-half to three-quarters of the length 32 of the pad 23.

The spring member 15 and the pad 23, respectively, include ends 33 and 34. The ends 33 of the spring member 15 are located inwardly from the ends 34 of the pad member 23.

ADHESIVE & LINER

The adhesive 26 is located between the spring member 15 and the backing of the pad 23 such that the entire engaging surface 18 of the spring member 15 wholly adheres with the pad 23.

In the embodiments using a transparent or clear pad 23, it is desirable to have the adhesive 26 substantially clear in color. This is particularly the case where there is an imprintation 118 on the spring surface 18.

A surface perimeter area 30 of the pad 23 is formed between the outer edge 16 of the spring member 15 and the peripheral edge 25 of the pad 23. The surface perimeter area 30 includes the adhesive 26 for adhering to skin of the nose 14.

The surface area 17 of the spring 15 includes an adhesive carrier 20 for adhering to the skin of the nose 14.

The adhesive system is preferably No. 1509, Double Coated Medical Tape on Liner from 3M Company, 3M Center, St. Paul, Minn. This product is a double-coated transparent polyethylene film, coated on both sides with a hypoallergenic, pressure-sensitive, acrylate adhesive, supplied on a paper liner. The double coated tape is wound with the liner on the outside of the roll.

The carrier is transparent 3 mil polyethylene film; the adhesive is hypoallergenic, pressure-sensitive acrylate; and the liner is bleached Kraft-Glassine paper, silicone coated on both sides.

USING THE DILATOR

When the spring member 15 is located over the bridge 19 of the nose 14, the opposite flat surfaces 17 and 18 of the spring member 15 extend over the bridge 19 of the nose 14 and at least partly beyond the bridge 19 on both sides of the bridge 19.

In use on the nose 14, there are only the spring member 15, and the adhesive pad 23. There is the adhesive 26 between the pad 23 and the spring member 15, and selectively, in one form of the invention there is also the adhesive carrier 20 on the surface 17 of the spring member 15.

When the pad member 23 is located on the nose 14 of a wearer, the ends 33 of the spring 15 are urged outwardly as indicated by arrows 35 to separate from the skin covering the nasal passages 11 of the wearer. The pad 23 is lifted in part from the nasal passages 12 and 13 in the vicinity of the ends 33 of the spring member 15. When in position on the nose 14, a flat surface 17 of the spring member 15 engages directly on the nose 14 through an adhesive 22.

Figure 3:
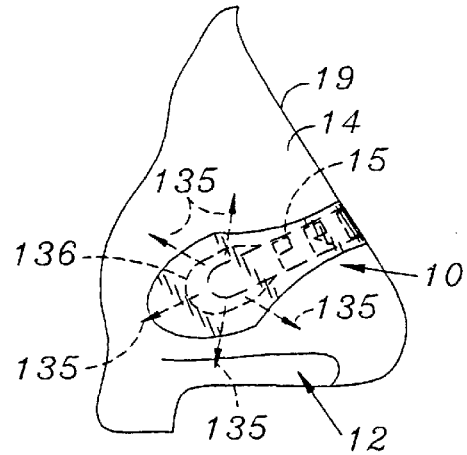
FIG. 3 is a side view of the dilator on the nose.
Figure 7:
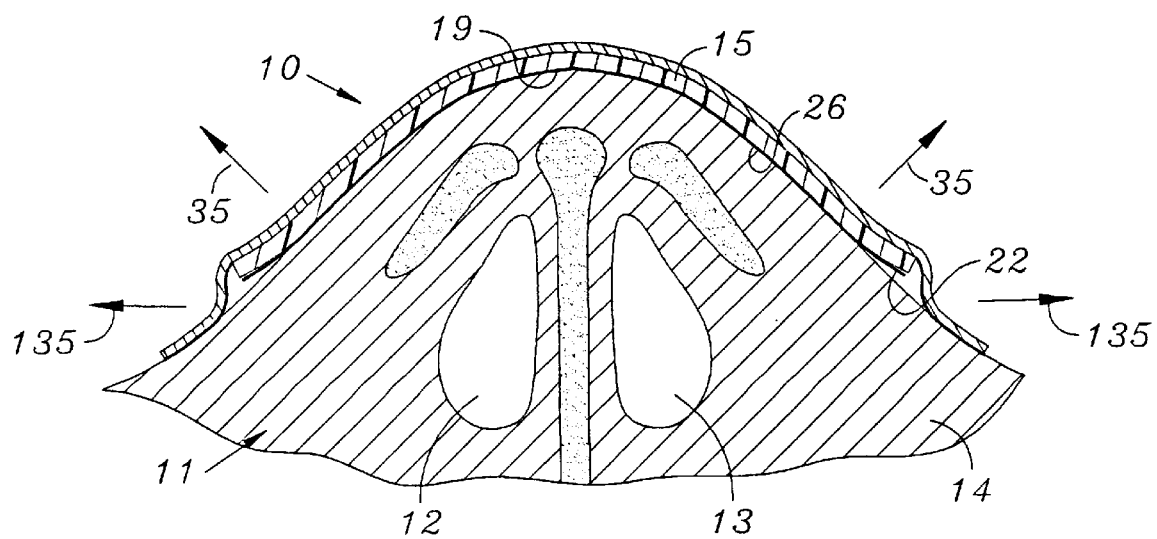
FIG. 7 is a cross-sectional view through the nose showing a dilator in position on the nose and the nasal passages opened.

Also as shown in FIGS. 3 and 7, there is a force 135 which is applied to the skin of the nose 14 from positions along a line 136 where the pad adheres to the nasal skin. This line 136 is slightly removed from the perimeter of the spring 15, and the force 135 is directed at different angles from the nose. The pulling force 135 is spread broadly around the nasal skin and increases the overall opening force on the nasal passages 12 and 13.

DILATOR PRIOR TO USAGE

When unattached to the nose 14, the spring member 15 and pad 23 have a natural position contrary to a curvature formed by location of the spring member 15 over the bridge 19 of the nose 14 and adjacent to the nasal passages 12 and 13. The resilient spring member 15 and pad 23 preferably have a position with a curvature 36 contrary to the shape of the curvature 37 formed from one nasal passage 12 over the bridge 19 to the second nasal passage 13. The contrary curvature 36 acts to place an increased amount of spring action on the dilator 10 so that the dilation action on the nasal passages 12 and 13 is enhanced when in use. The increased spring action is caused by the counter stress put into the spring member 15 prior to usage by the position of contrary curvature.

The dilator 10 is located in a package 38 before usage on the nose. The interaction of the walls 141 and 40 of the package 38 on the dilator 10 develops the contrary curvature 36. The shape of the package 38 is such that there is an effective curvature created by the surfaces 144 engaging the dilators 10 when packed. This curvature is a counter curvature 36 relative to the curvature 37 when in use. The wall 141 is loaded by spring 142 to ensure the counter curvature.

Figure 2:
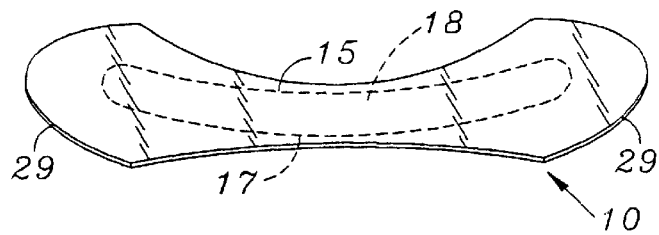
FIG. 2 is a perspective view from the top of the dilator before being placed on the nose.
Figure 4:
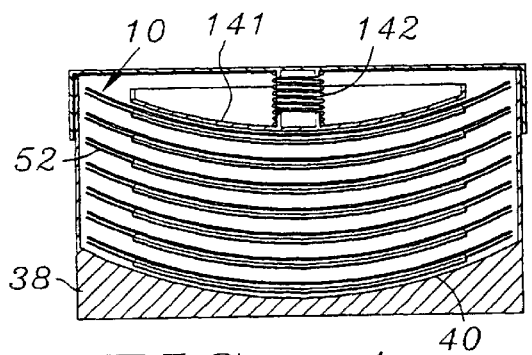
FIG. 4 is a view of multiple dilators in a package to effect the curvature contrary to the position of the dilator on the nose.
Figure 5:
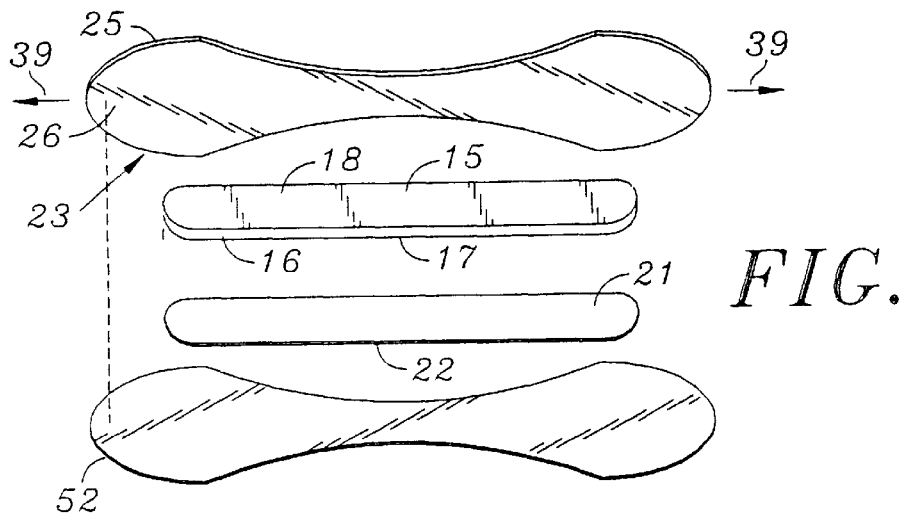
FIG. 5 is an exploded perspective top view of the components making up the dilator.
Figure 6:
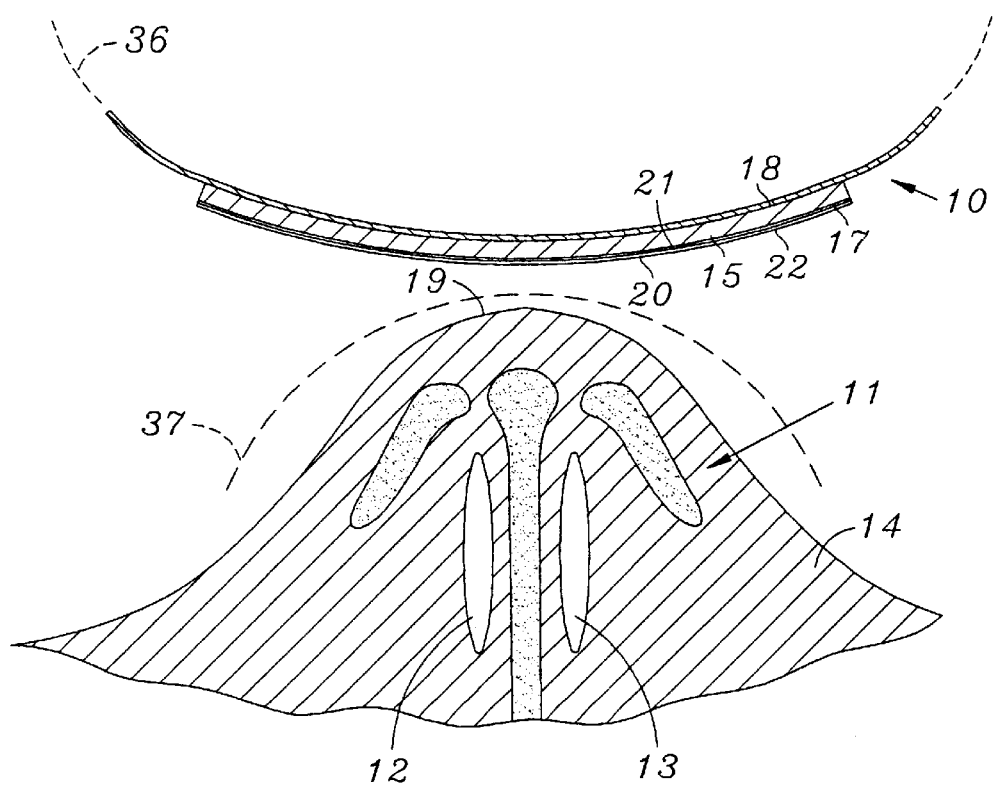
FIG. 6 is a cross-sectional view through the nose showing a dilator in a relative position before usage and the nasal passages closed.

Alternatively or additionally, the pad 23 is stretched prior to adhering to the spring 15. The stretch 39 (FIG. 5) acts to place the contrary curvature 36 onto the dilator 10 as explained in relation to FIG. 8. As the pad material 23 returns to its unstretched mode after the die-cut 46 it causes the spring 15 which adhered to the pad to be pulled into the counter curvature position 36. This is shown in FIGS. 2 and 10A.

MANUFACTURING THE DILATOR

The method of manufacturing for the dilator 10 requires the resilient spring member 15 to be die cut and located as an island within the surface area 30 of the pad 23.

The various materials: spring 15, pad 23, and adhesive 20, are provided, respectively, on rolls 41, 42 and 43 of material.

The resilient spring 15 is formed of a ribbon material 44 which is die cut at 45 from ribbon material 44.

Figure 8:
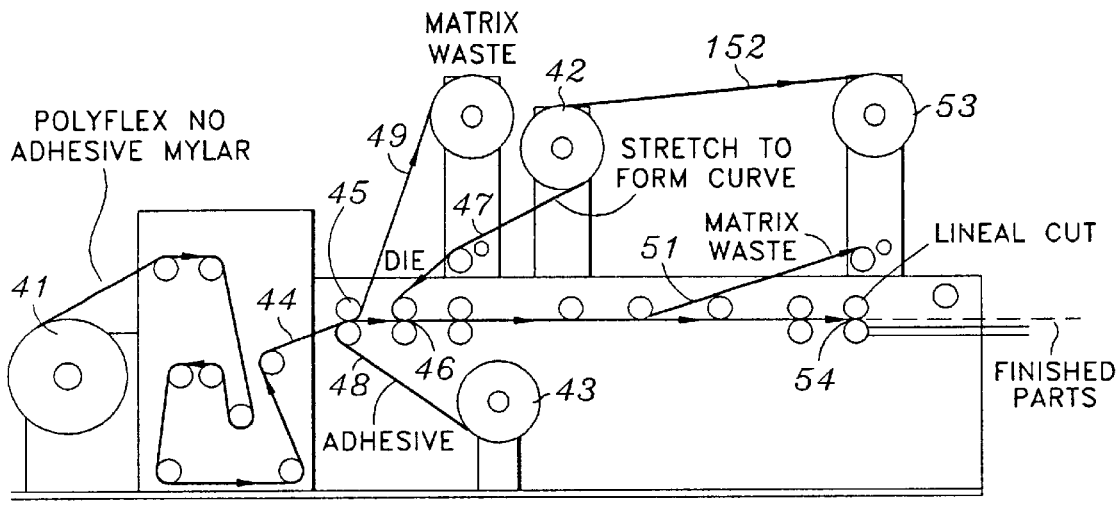
FIG. 8 is a diagrammatic view of a construction procedure for manufacturing the dilator where a stretch is placed on the pad to effect the contrary curvature.

The pad 23 is die cut at 46 from a second ribbon 47 of material. The release liner 152 removed from the pad 23 is removed as a ribbon to the waste liner roll 53. If the ribbon 47 is stretched between roll 42 and the die cut station 46, the structure is created to permit for the counter curvature configuration (FIG. 8).

The ribbon of resilient material 44 and pad material 47 are adhesively joined together in a webbing operation. The adhesive material 43 in the form of a ribbon 48 is fed into a position at die 45 on one side of the ribbon material 44 so as to place an adhesive on the ribbon material 44 for the spring. The adhesive system 20 is cut at die 45 to conform with the spring 15.

Adhesive 26 on the one side of the pad ribbon material 47 sticks the spring ribbon material 44 to the pad ribbon material 47 at the die 46.

Figure 8A:
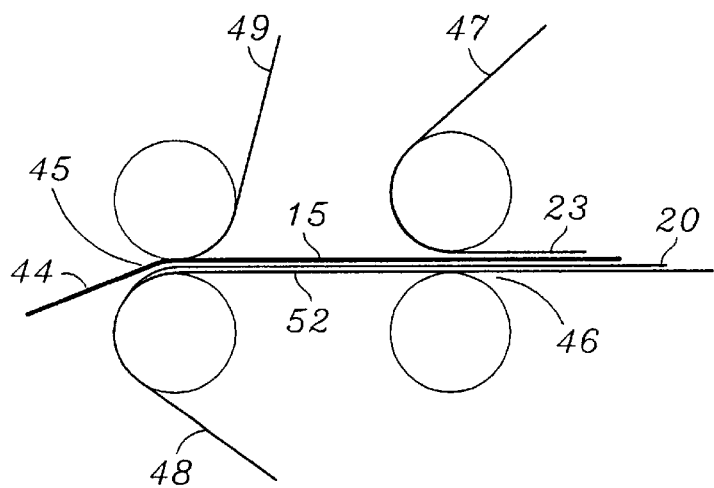
FIG. 8A illustrates side views of the dilator respectively at two different die positions in the construction procedure.

Non-adhering materials, 49, and 51 removed from the respective die cuts 45 and 46 are removed as ribbons of waste material. The material 49 is the unused ribbon material 44, namely the unused resilient material, and unused adhesive 48 which is die-cut 45. The material 51 is the spring 15, the pad 23, and the adhesive 20 which is die-cut 46. FIG. 8A illustrates the sandwiched components of the dilator at the die positions 45 and 46 respectively.

A liner 52 is also provided to cover the adhesive 26 of the pad 23 not covered by the spring 15. The liner is the leftover after the die-cut 45 of the resilient adhesive combination. When in use, the liner 52 is removed to expose the adhesive surface 26 and spring 15. The liner 52 is formed as the paper backing for the two sided adhesive 21 and 22 on carrier 20. The liner 52 is formed as the base of the roll of material 43 for the adhesive ribbon 48.

In some cases, the adhesive ribbon material 48 affixed to the spring ribbon material 44 may be avoided. There may be only the adhesive pad material 47 and the spring ribbon material 44 and a liner provided by a different ribbon material from roll 43. Thus only a paper type liner may be provided from roll 43. In such a situation there is no two sided coated tape.

Multiple dilators 10 are formed in a nested series in the manufacturing process through dies 45 and 46. They are then cut and separated at die 54 prior to packaging.

GENERAL

Many other forms of the invention exist, each differing from others in matters of detail only.

In some cases, the dilator prior to use is planar.

For instance, in some uses of the dilator on the nose, there are may be elements in addition to the basic spring member, the adhesive pad, and the adhesive between the spring and the nose skin. Also, there are situations where the adhesive on the spring for engaging the nose is unnecessary.

In other situations the position of curvature is one which means the pad is non-planar. Thus there could be situations where the curvature is generally along the shape of the nose, but not conforming to the nose. These situations could be, for instance, where a lesser degree of tension is needed to be placed on the nasal passages.

In one aspect of the nasal dilator 10, all the components located on the nose 14 are substantially transparent or clear. Thus, the spring 15 is transparent as are the adhesive carrier 20 and adhesive layers 21 and 22. So too is the pad 23 and adhesive 26 transparent. Thus, when the dilator 10 is located on the nose, it substantially blends with the nose color and/or is substantially invisible. As such, the dilator 10 is a cosmetic improvement over prior dilators.

In other situations, the pad may be partly transparent, or translucent, so that the spring can be seen through the pad. In yet other situations, the pad and/or spring can be made of different target colors to provide colorful combinations of pad and spring.

Figure 9:
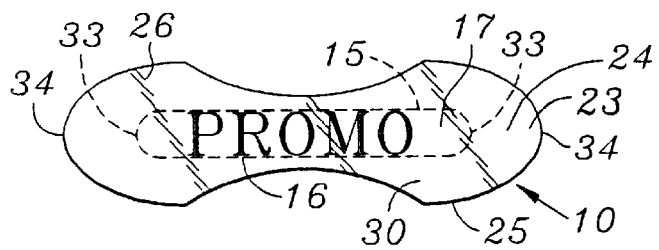
FIG. 9 is a top view of the dilator showing ornamentation on the pad, and wherein there is adhesive on the underside of the pad and on the underside of the spring, the undersides being for engagement on the skin of the nose.

In FIG. 9 the pad is ornamented with the word "PROMO." The pad is selectively not transparent, and the spring can not be seen when worn.

In FIG. 10A the pad is transparent and the spring can be seen. The one surface of the spring is ornamented with the word "PROMO" which can be seen through the transparent pad. There is a similar arrangement shown in FIGS. 10B, 3, and 11.

The dilator can be printed and/or tinted by any known process. This can be, for instance, silk screening, flexography, or gravure.

Although the invention in its mode with at least partly transparent components has been described with reference to two components, a pad and a spring with adhesive as required, there could be situations where there are multiple springs and/or pads. In some case, the springs may be located on the pad on the side removed from the nose. A further covering element may cover the spring.

The resilient member and other components of the dilator can be packaged in a bent, curved or straight condition, and can be in that static condition before dilator application to the nose.

In some other situations, instead of applying the adhesives on a 3 inch film, it can be coated onto the pad.

The invention is to be determined solely in terms of the following claims.

What is claimed is:

1. A nasal dilator for preventing outer wall tissue of nasal passages of a human nose from drawing in during breathing, comprising:

a unitary body including a single flexible pad having a surface area and peripheral edge, the unitary body having a pair of spaced apart end surfaces and a portion having an area of joinder between the spaced apart end surfaces, at least one spring member having opposite flat surfaces, the flexible pad being for engaging the at least one spring member secured thereto adjacent to at least each end surface, the unitary body being of non-uniform thickness and having a first thickness and a portion of greater thickness in an area of the flexible pad adjacent to the spring member, the unitary body being in a substantially planar state absent external forces applied thereto, such that the pair of spaced apart end surfaces which, if forced toward one another from initial positions within a plane of said unitary body to substantially reduce a direct spacing therebetween by a spacing reduction force external to said unitary body results in restoring forces in said unitary body tending to restore said direct spacing between said end surfaces, each of the end surfaces in area being at least about twice the area of the joinder portion between the end surfaces;

first adhesive means for securing the spring member at each end surface to the flexible pad such that one of the flat surfaces of the spring member adheres with the flexible pad at each end surface; and second adhesive means with said end surfaces of the flexible pad capable of engaging surfaces of nasal outer wall tissues sufficiently to remain so engaged against said restoring forces, such that the restoring forces in said unitary body tend to restore the unitary body to the substantially planar state and dilate a human's nose by urging outer wall tissues of such a human's nose outwardly with the end surfaces of said spring member, and also on release of the end surfaces from engagement with the outer wall tissue of such a human's nose the restoring forces further urging the unitary body to return to the substantially planar state, and the arrangement consisting of the flexible pad and spring member at the respective end surfaces for engaging nasal outer wall surfaces, and the adhesive means for adhering the unitary body to the outer wall tissues of a human's nose.

2. A nasal dilator of claim 1 wherein the area of joinder has a second peripheral edge, opposite the area of joinder from the at least one peripheral edge, said second peripheral edge also being a smooth concave peripheral line relative to the longitudinal axis of the unitary body.

3. A nasal dilator for preventing outer wall tissue of nasal passages of a human nose from drawing in during breathing, comprising:

a unitary body including a single flexible pad having a surface area and peripheral edge, the unitary body having a pair of spaced apart end surfaces and a portion having an area of joinder between the spaced apart end surfaces, the unitary body further having a longitudinal axis extending between the spaced apart end surfaces, at least one spring member, the flexible pad being for engaging the at least one spring member secured thereto adjacent to at least each end surface, the unitary body being of non-uniform thickness and having a first thickness and a portion of greater thickness in an area of the flexible pad adjacent to the spring member, the unitary body being in a substantially planar state absent external forces applied thereto, such that the pair of spaced apart end surfaces having a first initial position and a second initial position which, if forced toward one another from said first initial position and said second initial position within a plane of said unitary body to substantially reduce a direct spacing therebetween by a spacing reduction force external to said unitary body results in restoring forces in said unitary body tending to restore said direct spacing between said end surfaces, the area of joinder having at least one peripheral edge being a smooth concave peripheral line relative to the longitudinal axis of the unitary body;

first adhesive means for securing the spring member at each end surface to the flexible pad such that one of the flat surfaces of the spring member adheres with the flexible pad at each end surface; and second adhesive means with said end surfaces of the flexible pad capable of engaging surfaces of nasal outer wall tissues sufficiently to remain so engaged against said restoring forces, such that the restoring forces in said unitary body tend to restore the unitary body to the substantially planar state and dilate a human's nose by urging outer wall tissues of such a human's nose outwardly with the end surfaces of said spring member, and also on release of the end surfaces from engagement with the outer wall tissue of such a human's nose the restoring forces further urging the unitary body to return to the substantially planar state, and the arrangement being such that in use, there is only the spring member at the respective end surfaces, the flexible pad and the adhesive.

4. A nasal dilator of claim 3 wherein the area of joinder has a second peripheral edge, opposite the area of joinder from the at least one peripheral edge, said second peripheral edge also being a smooth concave peripheral line relative to the longitudinal axis of the unitary body.

5. A nasal dilator for preventing outer wall tissue of nasal passages of a human nose from drawing in during breathing, comprising:

a unitary body including a single flexible pad having a surface area and peripheral edge, the unitary body having a pair of spaced apart end surfaces and a portion having an area of joinder between the spaced apart end surfaces, the unitary body further having a longitudinal axis extending between the spaced apart end surfaces, at least one spring member, the flexible pad being for engaging the at least one spring member secured thereto adjacent to at least each end surface, the unitary body being of non-uniform thickness and having a first thickness and a portion of greater thickness in an area of the flexible pad adjacent to the spring member, the unitary body being in a substantially planar state absent external forces applied thereto, such that the pair of spaced apart end surfaces having a first initial position and a second initial position which, if forced toward one another from said first initial position and said second initial position within a plane of said unitary body to substantially reduce a direct spacing therebetween by a spacing reduction force external to said unitary body results in restoring forces in said unitary body tending to restore said direct spacing between said end surfaces, the area of joinder having at least one peripheral edge being a smooth concave peripheral line relative to the longitudinal axis of the unitary body;

first adhesive means for securing the spring member at each end surface to the flexible pad such that one of the flat surfaces of the spring member adheres with the flexible pad at each end surface; and second adhesive means with said end surfaces of the flexible pad capable of engaging surfaces of nasal outer wall tissues sufficiently to remain so engaged against said restoring forces, such that the restoring forces in said unitary body tend to restore the unitary body to the substantially planar state and dilate a human's nose by urging outer wall tissues of such a human's nose outwardly with the end surfaces of said spring member, and also on release of the end surfaces from engagement with the outer wall tissue of such a human's nose the restoring forces further urging the unitary body to return to the substantially planar state, and the arrangement consisting of the flexible pad and spring member at the respective end surfaces for engaging nasal outer wall surfaces, and the adhesive means for adhering the unitary body to the outer wall tissues of a human's nose.

* * * * *